US005543516A

United States Patent [19]

Ishida

[11] Patent Number: 5,543,516

[45] Date of Patent: Aug. 6, 1996

[54] PROCESS FOR PREPARATION OF BENZOXAZINE COMPOUNDS IN SOLVENTLESS SYSTEMS

[75] Inventor: Hatsuo Ishida, Shaker Heights, Ohio

[73] Assignee: Edison Polymer Innovation Corporation, Brecksville, Ohio

[21] Appl. No.: 245,478

[22] Filed: May 18, 1994

[51] Int. Cl.$^6$ ........................ C07D 265/14; C07D 265/16
[52] U.S. Cl. .................................................. 544/69; 544/90
[58] Field of Search ........................................ 544/69, 90

[56] References Cited

U.S. PATENT DOCUMENTS

| | | | |
|---|---|---|---|
| 5,152,939 | 10/1992 | Ishida | 264/29.1 |
| 5,266,695 | 11/1993 | Ishida | 544/73 |

FOREIGN PATENT DOCUMENTS 694489  7/1953  United Kingdom .

OTHER PUBLICATIONS

Kopf, P. W. and Wagner, F. R, "Formation and Cure of Novolacs: NMR Study of Transient Molecules", Journal of Polymer Science, Polymer Chemistry Edition, vol. 11, 1973, 939–960.

Primary Examiner—Mukund J. Shah
Assistant Examiner—Matthew V. Grumbling
Attorney, Agent, or Firm—Hudak & Shunk Co LPA

[57] ABSTRACT

A method for preparing a desired benzoxazine compound comprises preparing a substantially homogeneous reaction mixture that includes a phenolic compound; a primary amine; and an aldehyde, but no solvent other than for the solvency which the reactants may have for each other. Following its preparation, the reaction mixture is maintained at a temperature, and for a period sufficient to cause the reactants to combine chemically to form the desired compound.

5 Claims, No Drawings

PROCESS FOR PREPARATION OF BENZOXAZINE COMPOUNDS IN SOLVENTLESS SYSTEMS

TECHNICAL FIELD

This invention relates to a novel synthesis for benzoxazine compounds. More particularly, this invention relates to the preparation of benzoxazine compounds from phenolic derivatives, aldehydes, and primary amines. Specifically, this invention relates to the synthesis of benzoxazine compounds in systems that contain no solvents.

BACKGROUND OF THE INVENTION

Synthetic resins such as phenolic resins have enjoyed widespread use for many years. Such resins are obtained, for instance, from the condensation of phenol, or substituted phenols, with aldehydes such as formaldehyde, acid aldehyde, or furfural. Phenol-formaldehyde resins are typical of the group, constituting the chief class of phenolics, and when cured, the same are resistant to moisture, solvents, heat, and the like. Such resins are also dimensionally stable, have good electrical resistance, in addition to being noncombustible, and they possess good sound and noise absorbing characteristics. In view of these and other desirable properties, the resins find widespread use for fabricating molded and cast articles, in bonding powders, for ion exchange purposes, in laminating and impregnating operations, in manufacturing composites and electrical components, as well as many other areas.

While phenolic resins have been employed satisfactorily in the areas mentioned, they are not without certain drawbacks. For example, since their synthesis involves a condensation-type polymerization, they produce condensation by-products, which in many applications are a distinct disadvantage. Furthermore, in the case of the preparation of Novolak resins, for example, the synthesis depends upon the use of undesirable strong acid catalysts.

As a consequence of the foregoing and other disadvantages, in some instances, resort has been had to resins prepared from monomeric benzoxazine compounds, since they not only eliminate the need to use strong acid catalysts, but inasmuch as their polymerization is accomplished through the use of a ring-opening polymerization, they do not involve the generation of objectionable condensation byproducts. Furthermore, they are characterized by possessing a relatively long shelf life, and in addition, they offer considerable molecular-design flexibility, and have comparatively low viscosities, the latter property being one which is beneficial in processing them into desired products. In view of the many advantages derived from the use of benzoxazine compounds, their employment in the preparation of resins has become increasingly attractive.

Until now, however, benzoxazine resins have commonly been synthesized by dissolving the components necessary for their preparation, that is the phenolic derivative, an aldehyde, and a primary amine in a suitable solvent such as dioxan, toluene, alcohol, and the like. Such a synthesis is shown, for example, in British Patent No. 694,489 in which 3,4-dihydro-1,3 benzoxazine is said to be preparable in a solvent such as dioxan or in a lower aliphatic, water miscible alcohol, for example, methanol or ethanol, from paraformaldehyde in combination with certain substituted phenols and aliphatic primary amines. The desired product is subsequently isolated from the solvent medium by evaporation of the solvent, or by precipitating the synthesized product from solution through the addition to the reaction mixture of a suitable non-solvent.

Similarly, U.S. Pat. Nos. 5,152,939 and 5,266,695 are concerned with carbon-carbon composites prepared from benzoxazine compounds formed in solutions in which the reactive components are dissolved.

While the preparation of benzoxazine compounds from reaction mixtures in which the reactive components are present in solution has previously been used, such methods are not without difficulties. For example, it usually takes a relatively long time, i.e., at least several hours, to carry out the desired reaction, and to separate the reaction products from the solvent present. Furthermore, additional time is required if purification is necessary, as is often the case. In addition, although the yield of benzoxazines is satisfactory in reactions where solvents are present, the solvents pose toxicity risks, which in many cases require expensive measures to eliminate, for instance the installation of costly solvent recovery systems. Still further, as a consequence of the cost of replacing fugitive solvents, and for other reasons, the elimination of solvents from the reaction mixture altogether would provide an important economy to the synthesis process.

In recognition of the health risks and cost disadvantages described, therefore, some effort has in the past been devoted to the preparation of solventless systems. Kopf and Wagner, for example, have prepared the benzoxazine of 2,4-xylenol by heating hexamethylenetetramine and 2,4 xylenol in air for 2½ hours. However, this method is relatively expensive since it involves two stages, the first of which requires the synthesis of hexamethylene tetraamine from ammonium and formaldehyde, and subsequently, a further reaction between hexamethylene tetraamine and 2,4-xylenol; P. W. Kopf and E. R. Wagner, J. Polym. Sci., Polym. Chem. Edi. 11, 939 (1973). However, while solventless syntheses with two reactants are relatively common, a one-step synthesis for a product involving three reactants is unusual.

In view of the preceding, therefore, it is a first aspect of this invention to provide a solventless synthesis for the preparation of benzoxazine compounds in a solventless system.

A second aspect of this invention is to provide a single step method for the preparation of benzoxazine compounds.

Another aspect of this invention is to provide a solventless benzoxazine synthesis that is faster than a benzoxazine synthesis employing a solvent in the reaction mixture.

A further aspect of this invention is to provide a solventless benzoxazine synthesis in which the yield of benzoxazine is substantially as good as a benzoxazine synthesis that requires the use of a solvent medium to dissolve the reaction components.

An additional aspect of the invention is to provide a benzoxazine synthesis in which toxic solvents are eliminated.

Yet another aspect of this invention is to provide a benzoxazine synthesis which has fewer byproducts than a comparable synthesis in which, however, a solvent is employed in the reaction mixture.

A still further aspect of this invention is to provide a reaction mixture for synthesizing benzoxazine in which the concentration of reactants in the reaction mixture is maximized.

Still another aspect of this invention is to provide a continuous method for synthesizing benzoxazines in the absence of a solvent medium.

BRIEF DESCRIPTION OF THE INVENTION

The preceding and still further aspects of the invention are provided by a method for preparing a benzoxazine compound comprising a reaction mixture, solvent-less other than for the solvency which the reactants may have for each other, a phenolic compound, a primary amine and an aldehyde. After combining the reactants, the reaction mixture is desirably heated or cooled until the desired benzoxazine has been formed.

The preceding and still other aspects of the invention are provided by a continuous method for preparing a benzoxazine compound comprising a reaction mixture, solventless other than for the solvency which the reactants may have for each other, a phenolic compound, a primary amine and an aldehyde. The reaction mixture is subsequently charged into a screw extruder or a static mixer whose speed is adjusted to provide a residence time sufficient to allow the reactants to chemically combine, before being extruded.

DETAILED DESCRIPTION OF THE INVENTION

As previously indicated, until now, benzoxazine resins have been synthesized by dissolving three ingredients, i.e., a phenolic derivative, an aldehyde, and a primary amine in solvents such as dioxane, toluene, and alcohol. Typically, it takes more than several hours to complete the synthesis of the benzoxazine compound, due to the time necessary for the synthesis and subsequent drying of the solvent. Additional time is necessary if purification of the product is desired. While the yield of benzoxazine and molecular weight distribution using techniques employing a solvent are satisfactory, it is desirable to eliminate the use of solvents because of their toxicity. Also, economical advantages are gained by eliminating installation of a solvent recovery system, any need to take precautions because of solvent toxicity, and by reducing the number of required synthesis steps. As stated, the invention described herein is performed by carrying out the synthesis in the absence of a solvent, other than for any solvency which the reactants may have for each other, in a single step.

Typically, formaldehyde is marketed as a thirty-seven percent solution in water. In preparing a desired benzoxazine in a solvent system, the water solution of formaldehyde is combined with a solvent compatible with water, the solvent serving the function of dissolving the amine and phenolic components required for the benzoxazine reaction. However, the solvent reaction medium commonly has in the order of no more than about 10 percent by weight of the reacting components, which accounts for the fact that the reaction often requires some hours to complete.

In contrast, the solventless process which is the subject of the invention results in a reaction medium in which the reactive components comprise substantially 100 percent of the mixture, making it possible to carry out the reaction in minutes, rather than hours. The use of a non-solvent, heterogeneous reaction mixture rather than a homogeneous, solvent-containing system proceeds by a different mechanism, one in which the reaction kinetics are greatly altered, and in addition to being much more rapid, results in fewer unwanted intermediate structures and byproducts.

The following table is illustrative of the improvement in reaction times for the solventless synthesis of various di-functional benzoxazines, and the yields obtained for the times shown. As may be gathered from the table, the yields obtained from both methods, i.e., with and without solvent, have no significant differences; however, the reaction time is dramatically and unexpectedly shortened in the solventless procedure.

| | Yield of Benzoxazine vs. Time of Reaction | | | | |
|---|---|---|---|---|---|
| System | Sample 1*, % | Sample 2**, % | Sample 3***, % | Temp. °C. | Time |
| In Dioxane | 75% | 80% | 62% | Approx. 101.3 (Reflux) | 6 Hrs. |
| Solventless | 75% | 83% | 57% | Approx. 110° C. | 10 min. |

*2,2-bis(3,4-dihydro-3-toluidil-2H-1,3-benzoxazine)-propane
**2,2-bis(3,4-dihydro-3-phenyl-2H-1,3-benzoxazine)-propane
***2,2-bis-(3,4-dihydro-3-cyclohexyl-2H-1,3-benzoxazine)-propane While the synthesis is not limited to the benzoxazines illustrated, the process of the invention is useful in preparing mono-functional benzoxazines having the general formula:

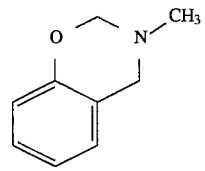

Di-functional benzoxazines having the following structure can also be synthesized:

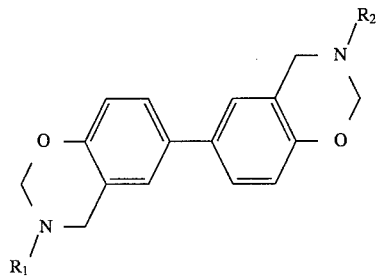

Other di-functional benzoxazines that can be formed include those having the following structure:

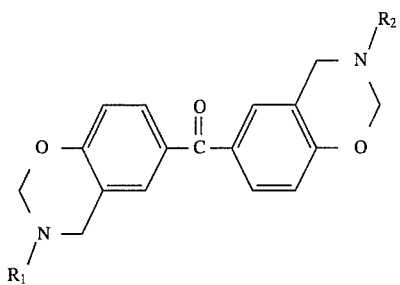

Still further di-functional benzoxazines that can be formed have the general formula

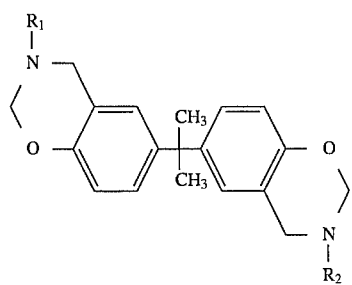

Yet other di-functional benzoxazines that can be produced by the process of the invention have the formula:

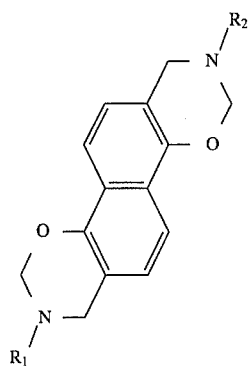

The procedure can also be used to prepare tri-functional benzoxazines, of which the following is an example:

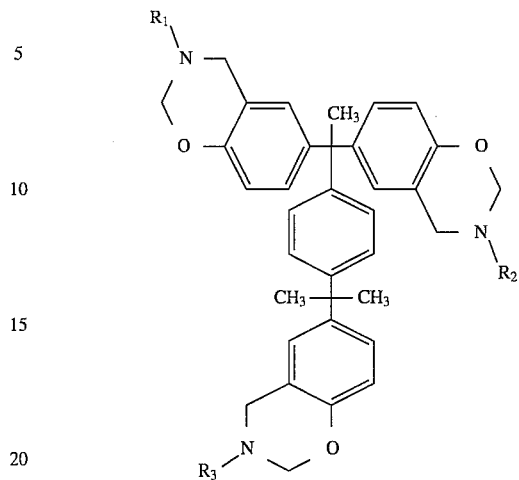

With respect to the structural formulas shown in the preceding, $R^1$ and $R^2$ are organic radicals that may be the same or different. Preferred radicals include alkyl groups, phenyl groups, saturated cyclic groups, siloxane groups, and others.

Referring to the above structures, the di-functional benzoxazines shown constitute a preferred embodiment of the invention. By way of example, the following di-functional compounds, as well as others, may all be prepared from the process disclosed herein.

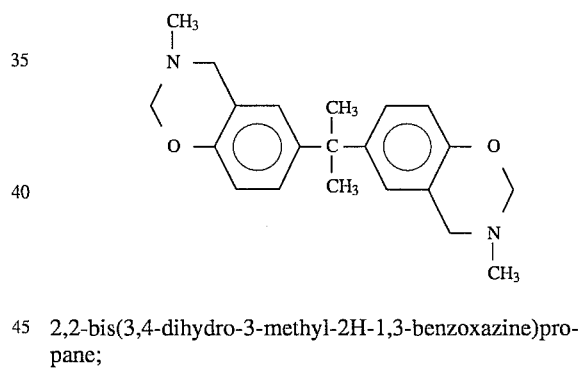

2,2-bis(3,4-dihydro-3-methyl-2H-1,3-benzoxazine)propane;

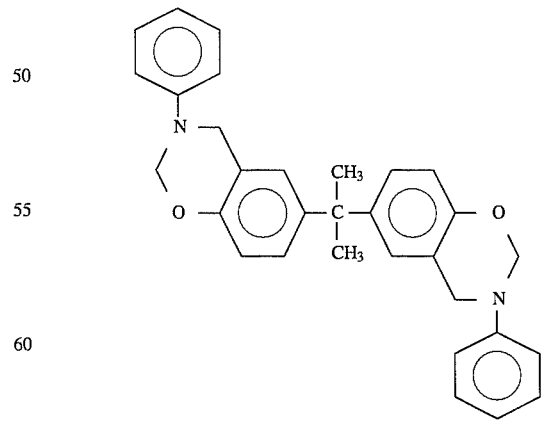

2,2-bis(3,4-dihydro-3-phenyl-2H-1,3-benzoxazine)propane;

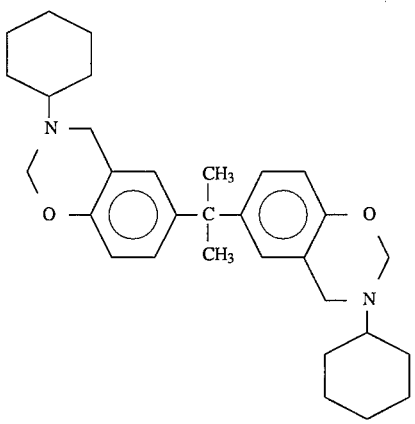

2,2-bis(3,4-dihydro-3-cyclohexyl-2H-1,3-benzoxazine)propane; and

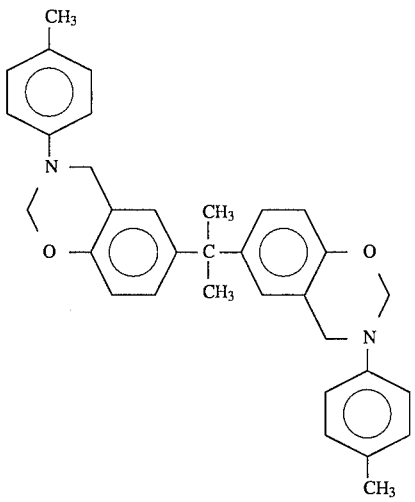

2,2-bis(3,4-dihydro-3-toluidil-2H-1,3-benzoxazine)propane.

Any of several methods may be used to carry out the solventless reaction; for example, in instances where the reactants, i.e., the aldehyde, the primary amine, and the phenolic compound are all solids, the solids may be physically mixed together, heated to their melting temperature, and thereafter maintained at a temperature sufficient to complete the interaction of the reactants so as to produce the benzoxazine desired in the time required.

Alternatively, as in the case where one or more of the reactants is a liquid, the reactants may simply be combined and heated to the point at which they all become liquid, either through melting, or by being dissolved in one or more of the liquid components present. The resulting mixture is then maintained at a temperature and for a period sufficient to bring about the desired reaction for the benzoxazine compound being synthesized.

While no catalyst is required for the reaction leading to the products previously described, if desired, for instance in order to change the composition of the products formed in the reaction mixture, acid catalysts such as HCl, or basic catalysts, for instance, NaOH, may be employed.

Insofar as the reactive components are concerned, any of various aldehydes may be employed for the synthesis, for example, vaporous formaldehyde; paraformaldehyde; polyoxymethylene; as well as aldehydes having the general formula RCHO, where R is aliphatic, including mixtures of such aldehydes.

Insofar as phenolic compounds are concerned, suitable compounds include,: for instance, those having the general formula

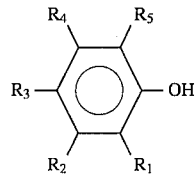

in which $R_1$ through $R_5$ are members selected from the group consisting of aliphatics, branched aliphatics, aromatics halogens, hydrogen or amines, and in which at least one of the ortho positions is unsubstituted.

One may use, for example, mono-functional phenols such as phenol; cresol; 2-bromo-4-methylphenol; 2-allyphenol; 1,4-aminophenol; or others.

Suitable di-functional phenols include phenolphthalane; biphenol; 4-4'-methylene-di-phenol; 4-4'-dihydroxybenzophenone; bisphenol-A; 1,8-dihydroxyanthraquinone; 1,6-dihydroxnaphthalene; 2,2'-dihydroxyazobenzene; resorcinol; fluorene bisphenol; and others.

Satisfactory tri-functional phenols comprise 1,3,5-trihydroxy benzene and others.

Polyvinyl phenol is also a suitable component for the benzoxazine compounds that constitute the subject of the invention.

With respect to the amines necessary for the reaction, the presence of a primary amine is required in order to obtain a benzoxazine ring structure. Suitable compounds include those having the general formula

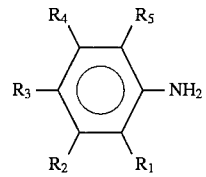

in which $R_1$ through $R_5$, which may be the same or different, are members selected from the group consisting of aliphatic substituents, and aromatic substituents, and further in which said substituents may include members selected from the group consisting of hydrogen, an amine, and a halogen. The amine compound may either be amine terminated, or the amine may be present in the form of a side chain on the compound. Silicones such as polydimethyl siloxane, as well as copolymers thereof which contain a primary amine group may all be employed. Illustrative of useful silicone compounds, are amine-functional silicones having the general formula

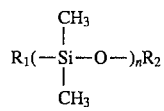

in which $R^1$ and $R_2$, which may be the same or different, are selected from hydrogen, a halogen, an aliphatic group, or an aromatic group, and in which at least one of $R_1$ and $R_2$ contains a primary amine group as a part thereof. Either monomeric or polymeric compounds having a primary amine included therein are satisfactory for producing the benzoxazine ring structure.

Examples of monofunctional amines include ammonium; methylamine; ethylamine; propylamine; butylamine; isopropylamine; octadecylamine; cyclohexylamine; alkylamine; 1-aminoanthracene; 4-aminobenzaldehyde; 4-aminobenzophenone; aminobiphenyl; 2-amino-5-bromopyridine; D-3-amino-e-caprolactam; 2-amino-2,6-dimethylpiperidine; 3-amino-9-ethylcarbazole; 4-(2-aminoethyl)morpholine; 2-aminofluorenone; 2-aminofluorene; 1-aminohomopiperidine; 9-aminophenanthrene; 1-aminopyrene; 4-bromoaniline; aniline; and others.

Suitable di-functional amines include 2-amino-benxylamine; 1,3-diaminopropane; 1,4-diaminobutane; 1,10-diaminodecane; 2,7-diaminofluorene; 1,4-diaminocyclohexane; 9,10-diaminophenanthrene; 1,4-diaminopiperazine; 1,4-methylenedianiline; 1,4-diaminobenzophenone; 4,4-diaminodiphenylsulfone; methylenedianiline; fluorenediamine; 4,4'-diaminodiphenylsulfide; 4,4'-oxydianiline; and others.

Suitable tri-functional amines include melamine, etc., while tetra-functional amines comprise fluorenetetraamine; tetraaminediphenylether; and the like.

Other suitable amines include amine-terminated polydimethylsiloxane and copolymers thereof; amine-terminated polybutadiene and its copolymers; polyallylamine; and others.

With respect to reaction conditions, the reaction can proceed at approximately room temperature given sufficient time, or the reaction temperature may be controlled as high as 250° C. in order to accelerate the reaction. In a preferred embodiment of the invention, the temperature of the reaction will be controlled at from about 0° C. to 150° C.

The reaction synthesis may be conducted at atmospheric pressure or at a pressure up to about 100 psi. In some instances, a reaction carried out under pressure constitutes a preferred mode since fewer byproducts are produced thereby, and where a polyfunctional benzoxazine is being prepared, relatively higher amounts of difunctional benzoxazine monomers are obtained.

The time of reaction will depend upon the nature of the reactants, as well as the reaction conditions. Commonly, however, a reaction time of about 15 to about 30 minutes is employed, although as stated, the reaction time may be either less or greater than that period, depending upon the circumstances of the reaction.

The relative amounts of the reactants required will depend upon their chemical nature, e.g., the number of reactive groups taking part in the reaction. The stoichiometry is well within the skills of those conversant with the art, and the required relative amounts of reactants are readily selected, depending upon the functionality of the reacting compounds.

In addition to the methods for carrying out the single step reaction already referred to, the reaction may also be carried out by using continuous processing machinery, for instance, screw extruders and static mixers. In this regard, it is possible to feed the unreacted components into the feed end of an extruder while maintaining the extruder at the desired reaction temperature. The extruder is operated at an RPM sufficient to provide the residence time required to carry out the chemical reaction within the extruder, and the finished benzoxazine product is automatically extruded at the conclusion of the reaction period.

The ultimate reaction mixture contains the desired benzoxazine monomer and oligomers thereof, as well as impurities. If desired, the mixture may be purified to obtain a more concentrated form of the product described, for example by well-known crystallization or solvent washing techniques. The resulting product can then be polymerized by heating the monomer, for instance, to from about 120° to 260° C. in instances where a polymerization catalyst is employed, the polymerization can be carried out at from about 100° to 220° C.

The following examples, while not to be construed as limiting in nature, are illustrative of the invention.

EXAMPLE 1

Aniline (27.9 g, 0.3 mole), 1,3,5-trihydroxybenzene (27.9 g, 0.1 mole), and paraformaldehyde (18 g, 0.6 mole) are mixed together in a mortar for 15 minutes until the powder is homogeneously mixed. The mixture is heated in a flask to above 100° C. and a clear solution is obtained. The resultant solution, which is constantly stirred by a magnetic stirrer, is heated at 130° C. for 15 min. The corresponding benzoxazine is obtained and the benzoxazine ring content is above 50 percent. A representative structure of the reaction product is shown as formulae (I).

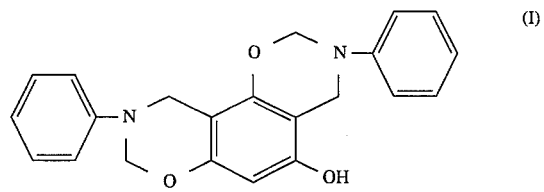

EXAMPLE 2

Aniline (18.6 g, 0.2 mole), polyvinylphenol (24 g, 0.01 mole) and paraformaldehyde (12 g, 0.4 mole) are mixed together and heated to 130° C. for 5 minutes. A viscous solution results. A slightly yellowish solution containing the polymer with an average poly-vinyl-(benzoxazine-co-phenol) structure, shown as formulae (II), is obtained. The relatively mild experimental conditions employed are selected to minimize crosslinking.

In another experiment, the same ingredients are heated at 130° C. for 10 minutes. The viscosity of this solution is somewhat lower than the solution heated for 5 minutes, although the benzoxazine content of the resultant polyfunctional material of the sample heated for 10 minutes is higher than the sample heated for 5 minutes. The sample becomes additionally viscous when heating is continued for more than 1 hour.

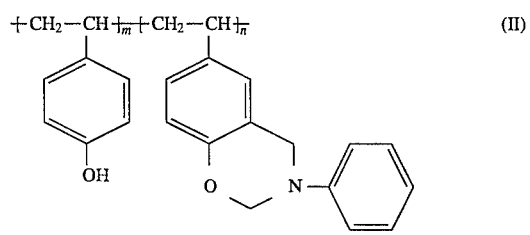

EXAMPLE 3

1,4-diaminobutane (8.8 g, 0.1 mole), phenol (18.8 g, 0.2 mole) and paraformaldehyde (12 g, 0.4 mole equivalent) are mixed together and heated to 100° C. The mixture readily becomes a homogeneous, clear liquid during the procedure. The solution is then heated, while stirring with a magnetic bar, in a flask to 120° C. for 20 minutes to afford the corresponding benzoxazine shown as formulae (III). The benzoxazine content realized is greater than 75 percent.

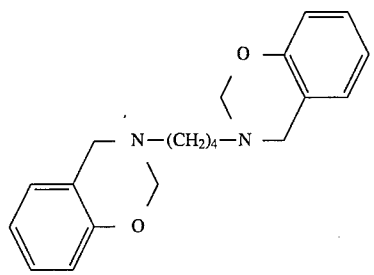

(III)

EXAMPLE 4

An amine-terminated polydimethylsiloxane (22 g, 0.01 mole), phenol (1.88 g, 0.02 mole) and paraformaldehyde (1.2 g, 0.04 mole equivalent) are mixed together and heated to 100° C. to obtain a viscous solution. The solution is heated during stirring to 130° C. for 20 min. Benzoxazine-terminated polydimethylsiloxane, as shown in formulae (IV), is obtained. There is no obvious viscosity change observed, although it is lowered somewhat. The benzoxazine yield obtained is greater than 80 percent.

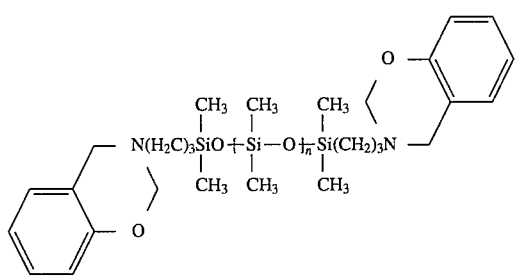

(IV)

EXAMPLE 5

1,4-diaminocyclohexane (11.4 g, 0.1 mole), phenol (18.8 g 0.2 mole), and paraformaldehyde (12 g, 0.4 mole) are mixed and heated to 100° C. to obtain a clear, homogeneous solution. The solution is then heated to 130° C. for about 15 minutes to obtain the corresponding benzoxazine, illustrated in formulae (V), incorporating cyclohexane groups. A good benzoxazine yield, i.e., greater than 85 percent, is obtained.

In another experiment, the identical solution is maintained at 110° C. for 1 hour. The same benzoxazine is formed, and the yield is similar to that obtained under the former reaction conditions.

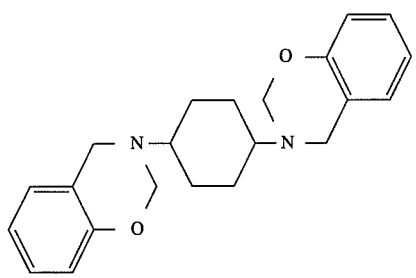

(V)

EXAMPLE 6

Aniline (9.3 g, 0.1 mole), 2-allylphenol (13.4 g, 0.01 mole), and paraformaldehyde (6 g, 0.2 mole) are mixed and heated to 110° C. for 30 min. A benzoxazine incorporating a reactive double bond, as shown in structure (VI), is obtained.

In another experiment, the same ingredients are mixed and magnetically stirred at 80° C. for approximately 2 hours. A significant benzoxazine yield is obtained.

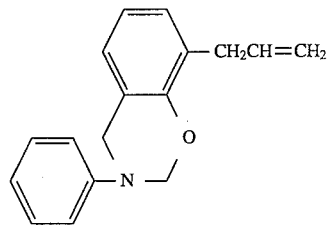

(VI)

EXAMPLE 7

In a synthesis of 2,2-bis(3,4-dihydro-3(4-methylphenyl)-2H-1,3-benzoxazine)propane, toluidine (0.21 g, 0.001 mole), bisphenol-A (0.23 g, 0.002 mole) and paraformaldehyde (0.12 g, 0.004 mole) are weighed and put into a mortar. The sample is thereafter ground and mixed with a pestle, and placed in a sample vial. The vial containing the sample is subsequently put into a preheated oven, and kept at 75° C. for 1 hour, or alternatively, at 110° C. for 20 minutes. The vial is subsequently cooled in an ice bath to yield a two layer solid, the upper layer being clear and yellow, while the lower layer is a white, opaque paste. Recrystallization of the product, maintained at 110° C., in ethyl ether affords a 0.2 g white powder. After evaporation of the solvent from the mother liquor, a yellow viscous liquid product is obtained. Recrystallization can also take place in ethyl acetate, tetrahydrofuran or acetone.

EXAMPLE 8

The reaction of Example 7 can also be carried out in a closed system as follows. Toluidine (0.21 g, 0.001 mole), bisphenol-A (0.23 g, 0.002 mole) and paraformaldehyde (0.12 g, 0.004 mole) are placed in a mortar, and the sample is ground and mixed with a pestle. Subsequently, the sample is put into a capillary whose open end is then sealed, and the vial put into an oven pre-heated to 75° C. The capillary is kept at 75° C. for 1 hour, and thereafter cooled in an ice bath to provide the desired product.

EXAMPLE 9

In another experiment, similar to Example 7, in which the reaction is carried on in a melt, toluidine (2.14 g, 0.02 mole), bisphenol-A (2.28 g, 0.01 mole) and paraformaldehyde (1.20 g, 0.04 mole) are put into a flask that has been preheated in an oil bath at 110° C., and melted. The mixture is then stirred with a magnetic stirrer for about 20 minutes at the same temperature. Within the first minute, the mixture has melted and become a light brown transparent liquid; after the liquid has boiled for about 20 minutes, however, it turns opaque and light yellow. The flask is thereafter cooled in an ice bath to produce the desired product. Recrystallization of the product, kept at 110° C. in ethyl ether, provides 0.2 g of a white powder. After evaporation of the mother liquor, a yellow, viscous liquid product is obtained.

EXAMPLE 10

In still another experiment, similar to Example 7, p-toluidine (21 g), bisphenol A (22.4 g), and paraformaldehyde (12 g) are mixed together. The mixture is heated to 155° C. and stirred for 15 min. with the solution becoming transparent above 130° C. The solution is then cooled down, dissolved in ether and kept at room temperature overnight. Upon cooling, the product precipitates and is removed by filtration.

EXAMPLE 11

In a further experiment, similar to Example 7, p-toluidine (21 g), bisphenol A (22.4 g), and paraformaldehyde (12 g) are mixed together and heated to 135°–140° C., the solution becoming transparent at 135° C. When the final product is dissolved in ether, two phases appear, i.e., a white solid phase, and a yellow ether liquid phase. The solid phase is removed by filtration, and then washed several times with ether to obtain a fine white powder, the yield of the monomer being 70 percent.

EXAMPLE 12

The benzoxazine of Example 7 is also prepared under pressure using an autoclave. In the experiment, p-Toluidine (21 g), bisphenol-A (22.4 g) and paraformaldehyde (12 g) are charged into an aluminum pan and the powder mixture heated in the autoclave at 110° C. for 30 min. at various pressures ranging from 5 to 120 psi, to provide the product.

EXAMPLE 13

In a scaled-up experiment, a Banbury mixer containing 100 g of the reactants of Example 7 is operated at temperatures between room temperature and 100° C. for 30 minutes. At a moderate temperature, the reactants melt to give a clear liquid, and produce the benzoxazine in a manner similar to the above melt method. However, due to the extensive mixing, the optimum temperature of the Banbury mixer method is lower than the laboratory glassware method.

EXAMPLE 14

Further scale-up to produce the product of Example 7 is undertaken using continuous processing equipment provided by connecting a single-screw extruder to a Brabender Plasticorder. The equipment is charged with 0.5 kg of the reactant mixture of Example 7 in a solid state, the composition of the solid mixture being present in a stoichiometric ratio. The extruder is operated between room temperature and 100° C., and its speed of rotation is adjusted to provide a residence time for the reactants of between 5 to 30 minutes, sufficient to produce the product.

EXAMPLE 15

In an experiment designed to produce 2,2-bis(3,4-dihydro-3-phenyl-2H-1,3-benzoxazine)propane, aniline (1.86 g, 0.02 mole), bisphenol-A (2.28 g, 0.01 mole) and paraformaldehyde (1.20 g, 0.04 mole) are placed in an Erlenmeyer flask which is then heated on a hot plate. The solid is dissolved in aniline at about 50° C., and the mixture is stirred with a magnetic stirrer for 20 minutes at 110°–120° C. to give a clear yellow liquid. The liquid is poured into an aluminum dish and then cooled to produce a yellow solid product.

EXAMPLE 16

In an additional experiment, aniline (18 g, 0.2 mole), bisphenol A (22.4 g, 0.1 mole), and paraformaldehyde (12 g, 0.4 mole) are mixed together for 15 min. At temperatures up to 100° C., the solution is hazy, but it becomes transparent above 100° C. The solution is stirred for 15–20 min. at a temperature of 130°–135° C. to produce the benzoxazine monomer of Example 7, the yield after purification being 71 percent.

EXAMPLE 17

In a further experiment, 2,2-bis(3,4-dihydro-3-methyl-2H-1,3-benzoxazine)propane is synthesized from a mixture of 1.5 ml (0.02 mole) 40 percent aqueous methylamine, 2.28 g (0.01 mole) of bisphenol-A and 1.20 g (0.04 mole) of paraformaldehyde, the reaction mixture being contained in an Erlenmeyer flask which is heated on a hot plate. The mixture is stirred with a magnetic stirrer for 10 minutes at 110° C. to give a white opaque paste that is then poured into an aluminum dish and cooled. The product obtained is a white solid.

EXAMPLE 18

In an experiment designed to produce 2,2-bis(3,4-dihydro-3-cyclohexyl-2H-1,3-benzoxazine)propane, cyclohexylamine (1.4 ml, 0.01 mole), phenol (0.94 g, 0.01 mole) and paraformaldehyde (0.60 g, 0.02 mole) are placed in an Erlenmeyer flask, which is heated on a hot plate. The solid dissolves in the cyclohexylamine at about 45° C. The mixture is stirred with a magnetic stirrer for 10 minutes at 110° C. to yield a clear yellow liquid. Afterward, the liquid is poured into a vial and cooled. A yellow liquid product is obtained.

EXAMPLE 19

In another experiment, cyclohexylamine (19.8 g), 2,4-dimethylphenol (24 ml), and pareformaldehyde (10 g) are mixed together for 15 min. at 85°–95° C. The solution becomes transparent at 80° C. The benzoxazine monomer yield after purification is about 69 percent.

While in accordance with the Patent Statutes, a preferred embodiment and best mode has been presented, the scope of the invention is not limited thereto, but rather is measured by the scope of the attached claims.

What is claimed is:

1. A method for preparing a benzoxazine compound comprising:

preparing a reaction mixture containing reactants including a phenolic compound, a primary amine, and an aldehyde, said reaction mixture containing no solvents for said reactants other than for the solvency which said reactants may have for each other;

bringing said reactants to a temperature at which the reactants combine chemically and maintaining them at that temperature to form said benzoxazine compound, said phenolic compound including one or more phenolic groups, said groups having the general formula:

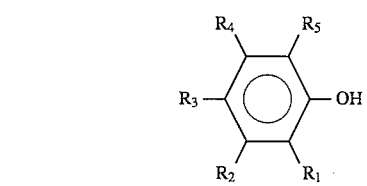

in which $R_2$ through $R_4$ are members selected from the group consisting of aliphatics, branched aliphatics, aromatics, halogens or amines, and in which $R_1$ and $R_5$ are selected from the group consisting of aliphatics, branched aliphatics, aromatics, halogens, hydrogen or amines provided that at least one of $R_1$ and/or $R_5$ must be hydrogen.

2. A method according to claim 1, wherein said primary amine has the general formula R—R'NH$_2$ in which R' is a structure selected from the group consisting of a linear structure, a branched structure, and a cyclic structure, and in which R is a member selected from the group consisting of hydrogen, halogen, methyl, vinyl, and an amine.

3. A method according to claim 2, wherein said primary amine has the general formula:

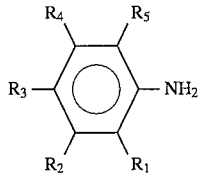

in which $R_1$ through $R_5$, which may be the same or different, are members selected from the group consisting of aliphatic substituents, and aromatic substituents, and further in which said substituents may include members selected from the group consisting of hydrogen, an amine, and a halogen.

4. A method according to claim 1, wherein said primary amine is an amine-functional silicone having the general formula:

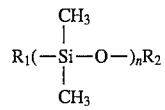

including copolymers thereof, in which $R_1$ and $R_2$, which may be the same or different, are members selected from the group consisting of hydrogen, a halogen, an aliphatic group, and an aromatic group, and in which at least one of said $R_1$ and $R_2$ contains a primary amine group as a part thereof.

5. A method according to claim 1, in which said reaction is carried out under a pressure greater than atmospheric.

* * * * *